(12) United States Patent
Kröckel

(10) Patent No.: US 7,123,010 B2
(45) Date of Patent: Oct. 17, 2006

(54) MAGNETIC RESONANCE APPARATUS AND OPERATION METHOD FOR HYPERTHERMIC TREATMENT

(75) Inventor: Horst Kröckel, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/482,093

(22) PCT Filed: Jun. 18, 2002

(86) PCT No.: PCT/DE02/02215

§ 371 (c)(1),
(2), (4) Date: Dec. 19, 2003

(87) PCT Pub. No.: WO03/002199

PCT Pub. Date: Jan. 9, 2003

(65) Prior Publication Data

US 2004/0199070 A1     Oct. 7, 2004

(30) Foreign Application Priority Data

Jun. 26, 2001  (DE) ............................. 101 30 619

(51) Int. Cl.
*G01V 3/00*  (2006.01)
*A61B 5/055*  (2006.01)
*A61N 5/02*  (2006.01)

(52) U.S. Cl. ............... 324/318; 324/307; 600/411; 600/412; 600/427

(58) Field of Classification Search ........... 324/307, 324/309, 318, 322; 600/410, 422, 411
See application file for complete search history.

(56) References Cited

U.S. PATENT DOCUMENTS

| 4,951,688 | A | * | 8/1990 | Keren ........................ 607/2 |
| 4,952,878 | A | * | 8/1990 | Mens et al. ............... 324/322 |
| 4,959,613 | A | * | 9/1990 | Yamamoto et al. ....... 324/318 |
| 5,185,573 | A | * | 2/1993 | Larson, III ................ 324/309 |
| 5,221,900 | A | * | 6/1993 | Larson, III ................ 324/307 |
| 5,252,922 | A | * | 10/1993 | Larson, III ................ 324/309 |
| 5,284,144 | A |   | 2/1994 | Delannoy et al. |
| 5,462,055 | A |   | 10/1995 | Casey et al. |
| 5,485,839 | A | * | 1/1996 | Aida et al. ............... 600/427 |
| 5,492,122 | A |   | 2/1996 | Button et al. |
| 5,543,711 | A | * | 8/1996 | Srinivasan et al. ....... 324/318 |
| 5,572,130 | A | * | 11/1996 | Ratzel ....................... 324/318 |

(Continued)

FOREIGN PATENT DOCUMENTS

DE   OS 197 07 451   8/1998
EP   0 560 397        9/1993

*Primary Examiner*—Diego Gutierrez
*Assistant Examiner*—Tiffany A. Fetzner
(74) *Attorney, Agent, or Firm*—Schiff Hardin LLP

(57) ABSTRACT

In a magnetic resonance system and operating method, antenna elements in an antenna array are disposed around an examination volume, and each antenna element has a separate transmission channel and reception channel associated therewith. The magnetic resonance apparatus is operated to obtain magnetic resonance signals, from which amplitude and phase information are derived for the individual antenna elements, and this information is used to subsequently operate the antenna elements in the array to emit RF energy with a predetermined phase and amplitude so as to generate focused RF energy for hyperthermic treatment. The magnetic resonance apparatus can also be used to obtain magnetic resonance signals in intervals which during which the hyperthermic treatment is interrupted, from which the temperature of the region being treated can be ascertained.

13 Claims, 3 Drawing Sheets

U.S. PATENT DOCUMENTS

| | | | |
|---|---|---|---|
| 5,661,401 A * | 8/1997 | Ishikawa et al. | 324/320 |
| 5,677,629 A * | 10/1997 | Borsboom | 324/318 |
| 5,786,692 A * | 7/1998 | Maier et al. | 324/307 |
| 5,830,142 A | 11/1998 | Kuhara | |
| 6,128,522 A * | 10/2000 | Acker et al. | 600/411 |
| 6,133,737 A * | 10/2000 | Greim | 324/318 |
| 6,236,208 B1 * | 5/2001 | Ham et al. | 324/318 |
| 6,351,124 B1 * | 2/2002 | Vester et al. | 324/318 |
| 6,549,799 B1 * | 4/2003 | Bock et al. | 600/422 |
| 6,624,633 B1 * | 9/2003 | Zou et al. | 324/318 |
| 6,904,323 B1 * | 6/2005 | Samulski | 607/101 |
| 2004/0199070 A1 * | 10/2004 | Krockel | 600/412 |
| 2004/0230263 A1 * | 11/2004 | Samulski | 607/101 |

* cited by examiner

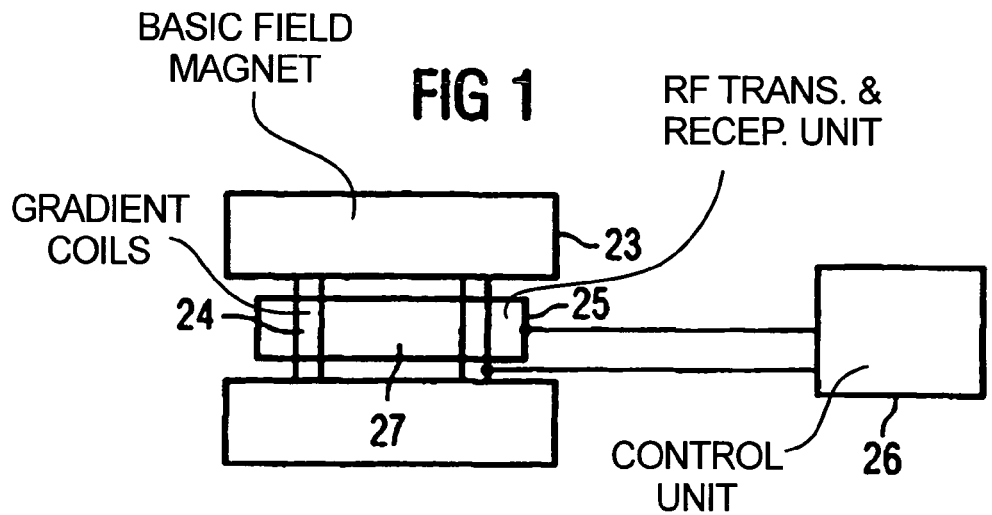
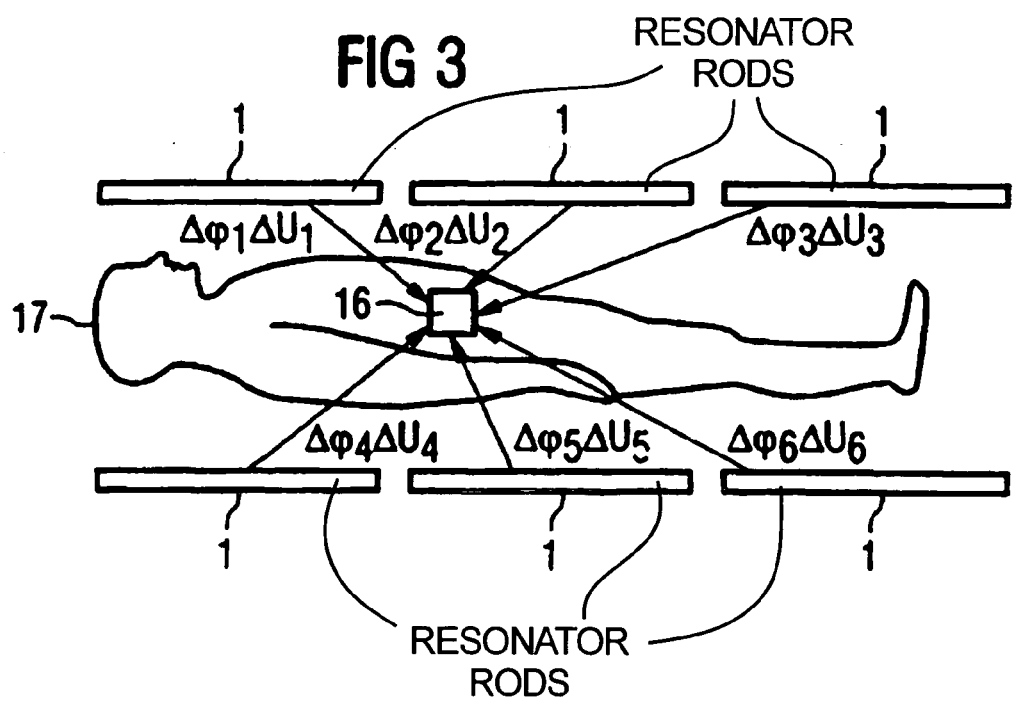

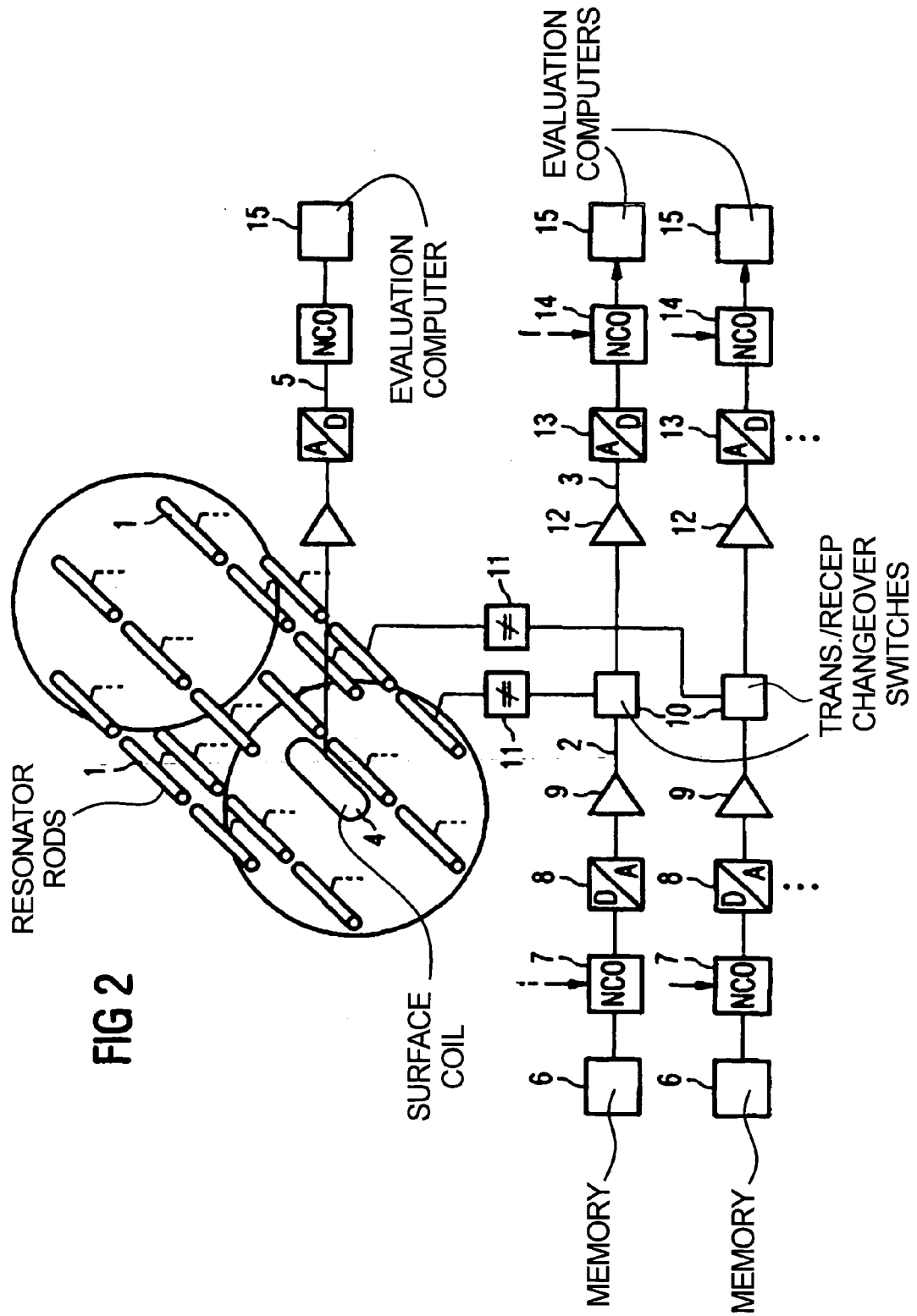

MAGNETIC RESONANCE APPARATUS AND OPERATION METHOD FOR HYPERTHERMIC TREATMENT

BACKGROUND OF THE INVENTION

1. Field of the Invention

The present invention relates to a magnetic resonance installation of the type having a basic field magnet, a number of gradient field coils, an RF transmission and reception unit and a control unit for actuating the gradient field coils and the RF transmission and reception unit for performing magnetic resonance measurements. The invention also relates to a method for operating such a magnetic resonance installation.

2. Description of the Prior Art

Magnetic resonance installations of the above general type are used in medical diagnosis in order to record images of the inside of a patient's body. Thus, magnetic resonance installations for imaging can be used, for example, in neurology, angiography or cardiology.

A frequent field of application for magnetic resonance tomography is the visualization or monitoring of tumors in cancer treatment. In the case of a recent technique for handling such tumors, chemotherapy or radiation treatment is supported or replaced by targeted heating of the tumor-containing region by means of focused irradiation with radio frequency (RF) energy. This recent technique is known by the term selective hyperthermia. With currently available hyperthermic appliances, the patient is positioned in a hyperthermic applicator, so that the region of the body that is to be treated is arranged approximately in the center below the applicator. The hyperthermic applicator is composed of a number of RF dipoles which are arranged in array form and are each supplied with pulsed or continuous RF power of defined amplitude and phase. The phase and amplitude of the radio frequency on each individual dipole are chosen such that the location of the region which is to be treated, i.e. of the tumor, is superimposed with the RF energy radiated from the individual dipoles such that the maximum field strength is achieved at that point. Some of the focused RF energy is absorbed by the tissue in the region of the tumor, so that this region is heated as a function of the radiated RF energy. Since the tumor-containing tissue is more heat sensitive than healthy tissue, the heating damages it to a greater extent than the surrounding healthy tissue. Such targeted heat treatment can cause the tumor-containing tissue to die.

A fundamental problem in hyperthermic treatment is the different propagation speed of electromagnetic waves in the tissue and in the surrounding air. Depending on the anatomy of the patient, the propagation path of the electromagnetic waves from the transmission dipoles to the tumor is filled by tissue or air to a greater or lesser extent. This influences the focusing, however, which means that it has not always been possible hitherto to focus the RF energy in optimum fashion during hyperthermic treatment without further auxiliary means. In the case of currently available hyperthermic appliances, the gap between the patient and the applicator is therefore filled with a water cushion which is filled with a special water solution after the patient has been positioned. This water cushion approximately aligns the propagation speeds of the RF radiation in the patient's body and between the body and the hyperthermic applicator, so that sufficiently good focusing is achieved even for different patient anatomies. However, this procedure is an unpleasant experience particularly for claustrophobic patients. In addition, simultaneous application of other applicators, for example for physiological monitoring of the patient during the hyperthermic treatment, is made more difficult by the water cushion, since little space remains for positioning additional applicators.

Hyperthermic treatment also requires the tissue temperature to be monitored during the treatment. This is currently achieved using special temperature sensors which are mounted on catheters. During the treatment, the catheters are inserted with the temperature sensors through the patient's skin and are taken to the irradiated tissue. This invasive method, however, puts an additional strain on the patient.

The search for improved techniques for recording the tissue temperature during hyperthermic treatment also takes the use of magnetic resonance measurements into consideration. The approach pursued in this context involves determining the temperature by means of a magnetic resonance examination which runs at the same time as the hyperthermic treatment. To this end, the hyperthermic applicator is placed in the examination space of a magnetic resonance installation and a magnetic resonance measurement is performed at the same time as the heating. The temperature of the tissue can be derived from the T1–T2 shift in the magnetic resonance signals obtained from the body region of interest.

One problem when applying a new approach to temperature measurement is the accuracy of the temperature measurement. This accuracy is currently barely sufficient, since the hyperthermic applicator is arranged between the RF transmission and reception unit of the magnetic resonance installation and the patient, which means that the received signal from a magnetic resonance echo is received only very weakly by the magnetic resonance installation's RF transmission and reception unit. In addition, the magnetic resonance signal is attenuated by the water cushions arranged between the hyperthermic applicator and the patient. Another cause of the insufficient accuracy of such temperature measurement is the choice of RF transmission frequency in the magnetic resonance installation. These magnetic resonance frequencies need to be sufficiently separated from the radio frequency of the hyperthermic applicator in order to decouple the magnetic resonance system from the hyperthermic system and to avoid mutual interference by the two systems. Known hyperthermic applicators operate in the frequency range of 100 MHz in order to achieve sufficient focusability for the radio frequency field in the patient's body. For this reason, the magnetic resonance frequencies are usually chosen in a range of 8–64 MHz in order to keep a sufficient separation from the 100 MHz of the hyperthermic applicator. To excite the magnetic resonance, however, the chosen magnetic resonance frequencies require magnetic field strengths in the basic field magnet of between 0.2 T and 1.5 T. At such basic field strengths, the temperature-dependent T1 T2 shift is not very distinct, however, which means that this also impairs the accuracy of the temperature determination.

SUMMARY OF THE INVENTION

An object of the present invention is to provide an apparatus for selective hyperthermic treatment which allows sufficient focusing of the RF field without the use of water cushions and strain-free temperature measurement with a high level of accuracy.

The above object is achieved in a magnetic resonance installation, having in a known manner, a basic field magnet, a number of gradient field coils, an RF transmission and reception unit and also a control unit for actuating the gradient field coils and the RF transmission and reception unit for performing magnetic resonance measurements. In contrast to known magnetic resonance installations, the RF transmission and reception unit has multiple antennas that are arranged in array formed around an examination space and that can be activated independently of one another using separate transmission channels for the purpose of emitting RF radiation of prescribable phase and amplitude. For each of the antennas, a separate reception channel is provided. The control unit, for each antenna, determines the amplitude and phase of a locally selective magnetic resonance signal received by the antenna and activates the antennas independently of one another for the purpose of emitting RF radiation of prescribable phase and amplitude in order to generate an RF field focused in the examination space for hyperthermic treatment.

In the inventive method for operating the magnetic resonance installation in the present case antennas and the gradient field coils initially are actuated for the purpose of performing a locally selective magnetic resonance measurement in the body which is to be examined. The magnetic resonance signals are received with the antennas, and the magnetic resonance signals received from the body region which is to be treated are evaluated by the control unit for each individual reception channel, i.e. for each individual antenna, according to amplitude and phase in order to detect the amplitude attenuation and phase shift in the radio frequency radiation on the path between the body region which is to be treated and each individual antenna. Next, the individual antennas are actuated independently of one another by the control unit using a suitable amplitude and phase and taking into account the detected amplitude attenuation and phase shift, in order to generate a correctly focused RF field for hyperthermic treatment at the location of the body region which is to be treated.

The present embodiment of the magnetic resonance installation and the above-described operating method allow hyperthermic treatment of a patient without a water cushion. Actuation of each individual antenna using the correct amplitude and phase for the purpose of correctly focusing the RF field is ascertained in advance by detecting the amplitude and phase of the magnetic resonance signal received by each individual antenna from the body region which is to be treated. In this way, regardless of the anatomy of the patient and the interspace between the antennas and the patient, the correct amplitude and phase actuation is always achieved for optimum focusing of the RF field at the location of a region which is to be treated, particularly a tumor. It is thus possible to provide additional applicators, for example for physiological monitoring of the patient during the hyperthermic treatment, while the same magnetic resonance installation can be used to perform a temperature measurement with a high level of accuracy and without any strain on the patient.

The present implementation of the magnetic resonance installation with the simultaneous option of locally selective hyperthermic treatment is achieved not by additional incorporation of a hyperthermic applicator but rather by simple redesign of existing components of a magnetic resonance installation. In this context, the one or more power transmitters for the antennas are designed such that they are firstly able to deliver the continuous power required for hyperthermic treatment, which is in the order of magnitude of 1–2 kW. Secondly, the power transmitters need to be designed such that they can deliver sufficient pulsed power for magnetic resonance measurements, i.e. pulsed powers in the order of magnitude of 20–30 kW. Preferably, this is achieved by replacing the customary pulsed power transmitters used in magnetic resonance installations with a larger number of power transmitters having a lower pulsed power per transmission channel.

The individual antennas are preferably in the form of resonance rods or elongate, electrically conductive material layers whose RF response is equivalent to that of resonance rods and which should have the smallest possible dimensions. The individual resonator rods are arranged around the cylindrical space for the patient. They are also equipped with a matching device which matches the impedance of the transmission path to the body region which is to be treated, which impedance is influenced by the patient and by the geometry in the examination space, to the line impedance of the supply line which connects the respective power amplifier to the resonator rod. The matching device can be equipped with a fixed transformation ratio or can be oriented to each patient by means of individual tuning.

In one embodiment of the present magnetic resonance installation, a separate power transmitter is provided for each antenna. Each of these power transmitters is equipped with a separate transmitter actuation circuit which allows phase control and amplitude control for the antenna. The actuation circuit should be able to generate any desired RF pulse shapes with widely differing pulse durations in order to allow both the magnetic resonance measurements with pulsed excitement and the hyperthermic treatment with continuous irradiation. Each of the transmitter actuation circuits preferably includes a modulator which is supplied from a discrete-value table via an analog/digital converter (ADC). The modulator can be in the form of an analog IQ modulator or a digital NCO. The frequency generation for the transmission frequency can be effected using a PLL or DDS loop. Such circuits for frequency generation are known to the person skilled in the art in the field of magnetic resonance installations.

In the case of the present magnetic resonance installation, each antenna also has a separate reception channel in order to be able to detect a magnetic resonance echo or signal which is induced in the antennas. To this end, the respective matching unit and the power amplifier preferably have a transmission/reception changeover switch arranged between them which forwards the magnetic resonance signal on each transmission antenna to a receiver circuit. The receiver circuit itself is produced by a preamplifier circuit and a demodulator circuit which can separate each individual received signal according to amplitude and phase. The receiver circuit can be equipped with an analog IQ demodulator or with a digital demodulator. This receiver circuit allows detection of the phase shifts and of the attenuation of the RF amplitude in the tissue surrounding the tumor.

The present magnetic resonance installation is designed to generate a sufficiently high magnetic resonance frequency which allows explicit focusing of the radio frequency field at the field strength of the basic field magnet. On the other hand, the field strength of the basic field magnet is chosen such that an explicit representation of the temperatures in the examined tissue is still achieved at the associated magnetic resonance frequency. For the field strength of the basic field magnet, a field strength of 3T is suitable, for example, which means that a magnetic resonance frequency of 123.2 MHz needs to be generated. This magnetic resonance frequency corresponds to a wavelength of 10–30 cm in the patient's body and 2.5 m in the air, which means that sufficiently intense focusing of the RF energy can be achieved.

The present magnetic resonance installation is preferably operated such that the irradiation with the RF energy to heat the desired body region is repeatedly interrupted briefly in order to perform a magnetic resonance measurement for the purpose of ascertaining the temperature in the body region in question. In this case, the temperature measurement is performed using a conventional magnetic resonance measurement with the antennas and subsequent evaluation of the T1–T2 shift. The local information is obtained in a known manner by means of the frequency and phase coding with the gradient field coils.

The temperature measurement is performed repeatedly in the course of the heating process in order to be able to avoid overheating of the region in question. The distances between the individual temperature measurements are chosen according to radiated RF power, duration of the irradiation and the body region. Depending on the type of the magnetic resonance measurement, i.e. according to the choice of pulse train, a range of a few 100 ms, particularly between 100 ms and 1 s, is provided for the temperature measurement. Between the temperature measurements, the RF energy is radiated again in order to heat the body region which is to be treated.

In one embodiment, a reception channel in the magnetic resonance installation is connected to a surface coil which allows a very good signal-to-noise ratio for the magnetic resonance measurements for determining temperature. In this regard, a receiver circuit is provided in addition to the surface coils, which are designed in line with the receiver circuits for the antennas of the RF transmission and reception unit. In this embodiment, the antennas of the RF transmission and reception unit and the surface coils are additionally equipped with a detuning device in order to prevent any interfering influence on the measurement by the currently unused part of the resonator. Such a detuning device is known from conventional magnetic resonance installations.

For optimum focusing of the RF field when carrying out the hyperthermic treatment, information is required about the phase shifts and the amplitude attenuation on the path from the individual antennas to the region of the patient's body which is to be treated, this information being different for each patient on an individual basis. To ascertain this information, the invention provides, as already stated, for the magnetic resonance installation to be used before the start of the heating sequence to produce a tuning sequence in which the magnetic resonance signals received from a prescribable body region are evaluated in terms of their amplitude and phase received on individual antennas. In one embodiment, this tuning sequence is in the form of an FID measurement, with suitable actuation of the gradient field coils being able to prevent the emission of echoes from regions of the body which are not of interest. Upon excitation, the tumor-containing region radiates RF energy in the form of magnetic resonance signals which are then intercepted by each antenna simultaneously. From a phase and amplitude differences, it is possible to derive the phases and amplitudes which are required for actuating the individual antennas in order to generate focused RF radiation in the tumor-containing body region. The antennas are then actuated using precisely these phases and amplitudes ascertained beforehand for each individual transmission antenna.

Such a magnetic resonance measurement for ascertaining the correct phases and amplitudes for actuating the antennas can naturally also be repeated while the heating sequence is being carried out, by virtue of said heating sequence being briefly interrupted for the magnetic resonance measurement. In this way, it is possible to attain optimum focusing results even if the patient changes position during the treatment.

DESCRIPTION OF THE DRAWINGS

FIG. 1 is a simplified illustration of the basic components of a magnetic resonance installation.

FIG. 2 schematically illustrates an exemplary embodiment of the RF transmission and reception unit in a magnetic resonance installation in accordance with the present invention.

FIG. 3 illustrates the superimposition of the RF fields respectively generated by the individual antennas in a tumor-containing body region of a patient, in accordance with the present invention.

DESCRIPTION OF THE PREFERRED EMBODIMENTS

Figure 4:
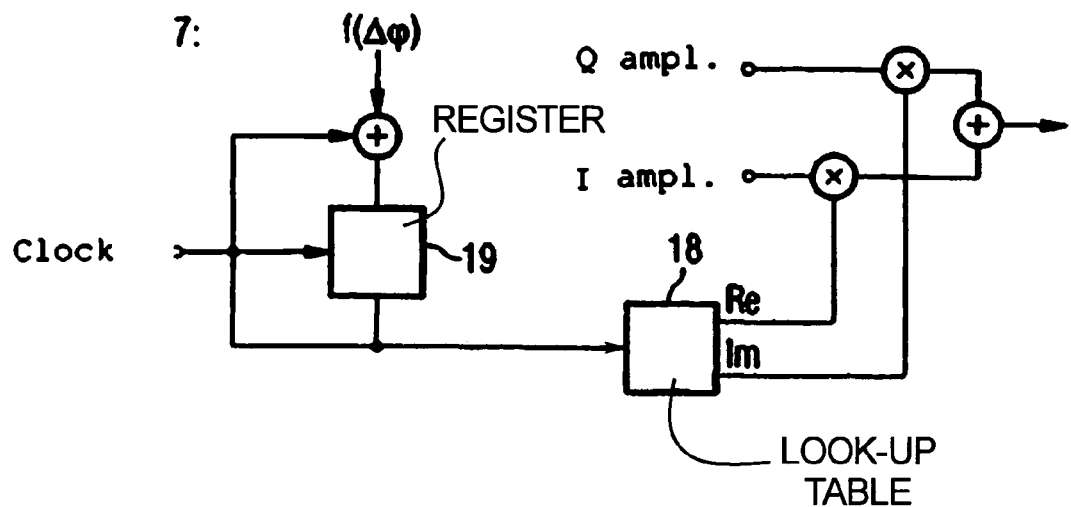
FIG. 4 illustrates an example of the operation of an NCO for generating RF signals with correct amplitude and phase in accordance with the present invention.

FIG. 1 shows a greatly simplified illustration of the basic design of a magnetic resonance installation in the form in which it is also produced for the present invention. FIG. 1 shows the basic field magnet 23, the gradient field coils 24, the RF transmission and reception unit 25 which surrounds the examination space 27, and also a control unit 26 for actuating the gradient field coils 24 and the RF transmission and reception unit 25. The units provided in magnetic resonance installations, such as evaluation computer, memory, pulse sequence controller, pulse shape generator or RF generator, are combined in the control unit 26 in this illustration.

FIG. 2 shows, as an example, an embodiment of an RF transmission and reception unit in the form in which it is used in a magnetic resonance installation based on the present invention. The RF transmission and reception unit is made up of a multiplicity of resonator rods 1 which are arranged in array form and are arranged around the cylindrical examination space 27 provided for the patient. Each of the individual resonator rods 1 is connected to a separate transmission channel 2 and to a separate reception channel 3. The figure indicates just two of these reception and transmission channels for two resonator rods by way of example. The transmission channel 2 comprises a memory 6 for storing the envelope and the phase profile for generating the RF excitation pulses. An NCO operated as a modulator 7 modulates the necessary pulse shape and phase onto a carrier frequency signal f which is obtained from a frequency generator (not shown). The signal is then converted in a digital/analog converter 8 and is amplified using the power amplifier 9. The RF signal amplified in this way is supplied to the resonator rod 1 via a tuning circuit 11 used for impedance matching. In this way, the individual resonator rods 1 are actuated independently of one another for the purpose of outputting RF radiation or RF pulses of defined phase and amplitude. If the intention is to ascertain the phase and amplitude required for each individual resonator rod for the purpose of focusing in a tumor-containing body region of a patient, then the individual resonator rods 1 are first actuated to output an RF pulse for exciting a magnetic resonance excitation signal in this body region. Then, or else at the same time as transmission, actuation of gradient fields limits the physical region from which the FID signal is emitted to the tumor-containing region. Next, the transmission/reception changeover switch 10 is changed over in order to switch the resonator rods 1 to reception or to connect them to the respective reception channel 3. The magnetic resonance signal is received by each of the resonator rods 1 and is supplied to an analog/digital converter 13 via a preamplifier 12. The digitized signal is split in an NCO 14, which is operated as a demodulator, according to the phase and amplitude and is supplied to an evaluation computer 15 which evaluates the amplitude and phase of the magnetic resonance signal for a particular body region in order to obtain for each of the resonator rods the amplitude and phase which is required for focusing. The individual resonator rods 1 are then actuated using the amplitudes and phases ascertained for them in order to achieve correct focusing in the tumor-containing body region. To this end, the transmission/reception switches 10 are set to the transmission channel again and the individual resonator rods 1 have a continuous RF power applied to them. This continuous power can also be composed of RF pulses.

This actuation with the correct phase and amplitude allows the RF energy to be focused in the tumor-containing body region 16 of the patient 17 without using water cushions, as indicated schematically in FIG. 3. To simplify matters, FIG. 3 indicates merely 6 resonator rods 1 which are actuated using different phase differences $\Delta\delta$ and amplitudes $\Delta U$ in order to output RF radiation.

FIG. 2 also shows a way of measuring temperature during the hyperthermic treatment. For this temperature measurement, the heating phase is briefly interrupted in order to generate an RF pulse using the resonator rods 1 for the purpose of exciting a magnetic resonance signal. The associated pulse sequence is known to the person skilled in the art from conventional magnetic resonance measurements. Optionally, a surface coil 4 can be positioned directly on the patient's body region of interest and can be connected to a separate reception channel 5 for the purpose of receiving the magnetic resonance signal. This reception channel 5, like the reception channels 3 for the resonator rods 1, has a preamplifier 12, an analog/digital converter 13 and an NCO 14 and is connected to the evaluation computer 15. Measuring the resonance signal for the temperature measurement using a surface coil has the advantage of a very good signal-to-noise ratio.

FIG. 4 shows an example of the interconnection of an NCO 7 as a modulator for the purpose of generating RF radiation of prescribable amplitude and phase. The NCO can also be operated in the opposite direction in order to demodulate a received signal. As shown in FIG. 4, a register 19 as an output connected to an adder to which the incoming frequency signal $f(\Delta\phi)$ is supplied. The output of the register 19 also serves as an input for a look-up table 18. The output of the look-up table 18 is the sine (Re) and cosine (Im) data stream described below.

The digital data streams, which represent a sine and cosine signal for the received RF signal in relation to a reference frequency, are generated in the same way as in the NCO, which is used for transmission. Instead of the adder, the received data stream digitized by the ADC is split over the two multipliers. One signal component is multiplied by a sine data stream, and the other is multiplied by a cosine data stream. When the two data streams have been subjected to digital low-pass filtering, the received RF signal is represented as a real-part component and an imaginary-part component in relation to the reference signal generated by the DDS (direct digital synthesis).

Figure 5:
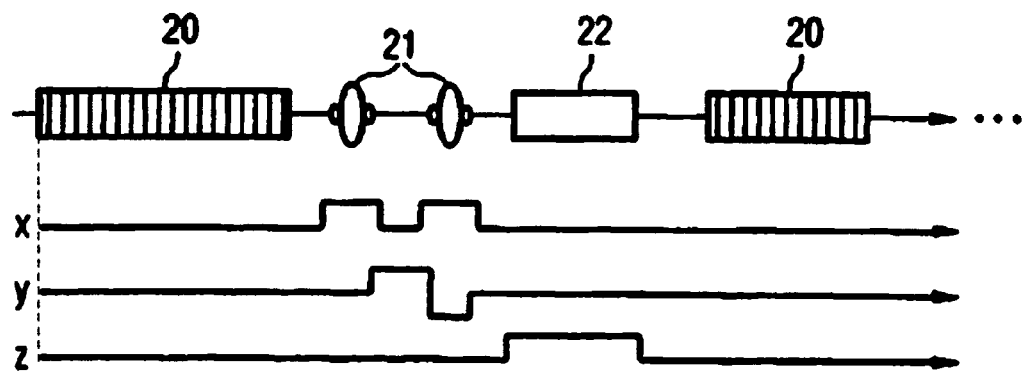
FIG. 5 shows an exemplary sequence for hyperthermic treatment, with simultaneous temperature measurement, in accordance with the invention.

Finally, FIG. 5 shows a control sequence for actuating the resonator rods 1 for the hyperthermic treatment. In the top part, the transmitted pulse 20 for heating the tissue can be seen. This heating sequence 20 is briefly interrupted in order to radiate an RF pulse train 21 for performing a magnetic resonance measurement in a known manner and then to receive the magnetic resonance signal using the individual resonator rods 1 during a defined reception time 22. After that, heating is continued with a fresh heating sequence 20. The bottom part of the figure schematically shows the actuation pulses for the gradient field coils for local coding in the x, y and z directions, as occur in the case of a spin echo sequence. Other sequence techniques which are not shown in this case can naturally also be used for this purpose.

In the time interval for which the heating sequence is briefly interrupted, it is possible to derive the temperature of the tissue in the body region of interest from the result of the magnetic resonance measurement.

The present system is able to implement all magnetic resonance applications which run at the radiated RF frequency. These applications are used in order to perform the anatomy representation or else spectroscopic measurements in the patient's region of interest and to measure the temperature distribution in the patient. In addition, the present system is able to actuate the individual resonator rods such that targeted focusing of the RF field is possible. In this context, the heating sequence is split into time slots in order to be able to interleave them with the magnetic resonance sequence for temperature measurement, so that temperature measurement can take place more or less simultaneously with the heating.

In this context, the frequency at which the magnetic resonance measurements are performed is at least approximately equivalent to the frequency at which the hyperthermic treatment takes place. This allows correct determination of the phase and amplitude with which each individual resonator rod needs to be actuated.

Although modifications and changes may be suggested by those skilled in the art, it is the invention of the inventor to embody within the patent warranted heron all changes and modifications as reasonably and properly come within the scope of his contribution to the art.

What is claimed is:

1. A magnetic resonance apparatus comprising:
   a basic field magnet that generates a basic magnetic field in an examination volume;
   at least one gradient coil that generates at least one gradient magnetic field in the examination volume;
   a plurality of radio-frequency antennas disposed in and forming a single array, around the examination volume, configured for radiating RF energy into, and receiving RF energy from, the examination volume;
   a plurality of separate transmission channels respectively connected to the plurality of RF antennas;
   a plurality of separate reception channels respectively connected to the plurality of RF antenna; and
   a control unit connected to said at least one gradient coil and to said single array of RF antennas for operating said at least one gradient coil and said single array of RF antennas in order to excite and acquire magnetic resonance signals having an amplitude and a phase, from the subject, said control unit determining, for each antenna in said plurality of RF antennas forming the single array, the amplitude and the phase of the magnetic resonance signal received by the respective antenna, and said control unit also activating the same plurality of RF antennas of said single array independently of each other in order to emit RF energy of a prescribed phase and amplitude into the examination volume in order to generate an RF field focused in the examination volume configured for hyperthermic treatment of the subject.

2. A magnetic resonance apparatus as claimed in claim 1 wherein each of said separate transmission channels comprises a power amplifier and a modulator.

3. A magnetic resonance apparatus as claimed in claim 1 wherein each antenna in said plurality of RF antennas is a resonator rod.

4. A magnetic resonance apparatus as claimed in claim 1 wherein said control unit interrupts generation of said focused RF field during hyperthermic treatment of the subject at predetermined times of an interval and, in said interval, activates said at least one gradient coil and at least one antenna in said plurality of RF antennas in order to acquire magnetic resonance signals indicating a temperature of a region of the subject in which said focused RF field is present.

5. A magnetic resonance apparatus as claimed in claim 1 wherein said subject in the examination volume has impedance characteristics associated therewith, and wherein said magnetic resonance apparatus comprises a matching circuit connected to said plurality of transmission channels that matches a line impedance of each transmission channel to said impedance characteristics.

6. A magnetic resonance apparatus as claimed in claim 1 wherein said array comprises a cylindrical arrangement of said plurality of RF antennas around said examination volume.

7. A magnetic resonance apparatus as claimed in claim 1 wherein said basic field magnet generates said basic magnetic field with a field strength of at least 2T.

8. A method for operating a magnetic resonance apparatus comprising the steps of:

operating a basic field magnet, at least one gradient coil, and a single RF antenna array comprised of a plurality of antenna elements, to radiate RF energy into, a body region of a patient disposed in an examination volume in order to excite magnetic resonance signals in said body region, said magnetic resonance signals containing location-dependent amplitude and phase information, and in order to receive said magnetic resonance signals from said body region;

from said location-dependent amplitude and phase information, automatically electronically determining, for each antenna element in the single antenna array, an amplitude and a phase required for emitting RF energy from that antenna element to produce focused RF energy from the single antenna array into the body region; and operating the same individual antenna elements of the single antenna array respectively with the determined amplitude and phase in order to emit said focused RF energy for a hyperthermia treatment in the body region.

9. A method as claimed in claim 8 comprising operating said at least one gradient coil and said antenna array in an FID control sequence to generate said magnetic resonance signals.

10. A method as claimed in claim 8 comprising repeatedly interrupting, for respective intervals, emission of the focused RF energy during the hyperthermic treatment and, in each of said intervals, operating said at least one gradient coil and said single antenna array to produce further magnetic resonance signals, and subsequently detecting said further magnetic resonance signals and determining a temperature of the body region from said further magnetic resonance signals.

11. A method as claimed in claim 10 comprising detecting said further magnetic resonance signals using surface coils separate from said single antenna array.

12. A method as claimed in claim 11 comprising operating said single antenna array to emit said RF energy at a frequency for generating said magnetic resonance signals, and operating said single antenna array to emit said focused RF energy, also at said same frequency, for said hyperthermic treatment.

13. A method as claimed in claim 8 comprising Interrupting emission of said focused RF energy from said antenna array for an interval during said hyperthermic treatment and, in said interval, obtaining further magnetic resonance signals from said body region containing updated amplitude and phase information, and re-determining the respective amplitudes and phases for the individual antennas of said array, for emitting said focused RF energy, from said updated amplitudes and phases.

* * * * *